United States Patent
Tang et al.

(10) Patent No.: US 7,311,898 B2
(45) Date of Patent: Dec. 25, 2007

(54) HIGH EFFICACY, LOW IRRITATION ALUMINUM SALTS AND RELATED PRODUCTS

(75) Inventors: Xiaozhong Tang, Bridgewater, NJ (US); Lin Fei, Kendall Park, NJ (US); Suman Chopra, Dayton, NJ (US); Peter Hilliard, Jr., Kendall Park, NJ (US)

(73) Assignee: Colgate-Palmolive Company, New York, NY (US)

( * ) Notice: Subject to any disclaimer, the term of this patent is extended or adjusted under 35 U.S.C. 154(b) by 403 days.

(21) Appl. No.: 11/080,913

(22) Filed: Mar. 15, 2005

(65) Prior Publication Data

US 2005/0158261 A1    Jul. 21, 2005

Related U.S. Application Data

(63) Continuation of application No. 10/314,712, filed on Dec. 9, 2002, now abandoned.

(51) Int. Cl.
*A61Q 15/00* (2006.01)
*A61K 8/00* (2006.01)
*A61K 8/02* (2006.01)

(52) U.S. Cl. .................. 424/65; 424/68; 424/400; 424/401

(58) Field of Classification Search .......... 424/65, 424/68, 400, 401
See application file for complete search history.

(56) References Cited

U.S. PATENT DOCUMENTS

| | | | |
|---|---|---|---|
| 4,025,615 A | 5/1977 | Rubino | |
| 4,058,597 A | 11/1977 | Passedouet et al. | |
| 4,331,609 A | 5/1982 | Orr | |
| 4,359,456 A | 11/1982 | Gosling et al. | |
| 4,435,382 A | 3/1984 | Shin et al. | |
| 4,499,069 A | 2/1985 | Krafton | |
| 4,606,915 A | 8/1986 | Rosenberg et al. | |
| 4,675,177 A | 6/1987 | Geary | |
| 4,775,528 A | 10/1988 | Callaghan et al. | |
| 4,871,525 A | 10/1989 | Giovanniello et al. | |
| 5,225,187 A | 7/1993 | Carmody | |
| 5,234,677 A | 8/1993 | Murray et al. | |
| 5,356,612 A | 10/1994 | Curtin et al. | |
| 5,384,117 A | 1/1995 | Vu et al. | |
| 5,393,518 A | 2/1995 | Kwass | |
| 5,516,511 A | 5/1996 | Motley et al. | |
| 5,518,714 A | 5/1996 | Park | |
| 5,589,196 A | 12/1996 | Callaghan et al. | |
| 5,595,729 A | 1/1997 | Barr et al. | |
| 5,599,533 A | 2/1997 | Stepniewski et al. | |
| 5,643,558 A | 7/1997 | Provancal et al. | |
| 5,718,876 A | 2/1998 | Parekh | |
| 5,908,616 A | 6/1999 | Parekh | |
| 5,997,850 A | 12/1999 | Tang et al. | |
| 6,024,945 A | 2/2000 | Parekh | |
| 6,066,314 A | 5/2000 | Tang | |
| 6,126,928 A | 10/2000 | Swaile | |
| 6,245,325 B1 | 6/2001 | Shen | |
| 6,265,364 B1 | 7/2001 | Kilpatrick-Liverman et al. | |
| 6,375,937 B1 | 4/2002 | Chopra et al. | |
| 6,436,381 B1 | 8/2002 | Carrillo et al. | |
| 6,682,749 B1 | 1/2004 | Potechin et al. | |
| 6,726,901 B2 | 4/2004 | Yin et al. | |
| 6,902,724 B1 | 6/2005 | Parekh et al. | |
| 6,911,195 B2 | 6/2005 | Vu et al. | |
| 6,969,510 B2 | 11/2005 | Holerca et al. | |
| 7,014,843 B2 | 3/2006 | Parekh et al. | |
| 7,105,691 B2 | 9/2006 | Holerca et al. | |
| 2004/0091436 A1 | 5/2004 | Li et al. | |
| 2006/0204463 A1 | 9/2006 | Tang et al. | |
| 2007/0110687 A1 | 5/2007 | Mattai et al. | |

FOREIGN PATENT DOCUMENTS

| | | |
|---|---|---|
| CA | 1153313 | 9/1983 |
| EP | 047650 A2 | 3/1982 |
| EP | 0499456 | 8/1992 |
| EP | 0653203 | 5/1995 |
| EP | 1005852 | 6/2000 |
| EP | 1005853 | 6/2000 |
| GB | 2076289 A | 12/1981 |
| GB | 1549555 | 11/1997 |
| WO | WO99/51192 A2 | 10/1999 |
| WO | WO 01/097768 A2 | 12/2001 |

OTHER PUBLICATIONS

CTFA International Cosmetic Ingredient Dictionary (Cosmetics, Toiletry & Fragrance Association, Inc., 7th Ed. 1997).

*Primary Examiner*—Shelley A. Dodson
(74) *Attorney, Agent, or Firm*—Michael F. Morgan

(57) ABSTRACT

A zirconium-free aluminum salt which: (a) has an aluminum to chloride molar ratio in the range of 0.5-2.5:1; (b) comprises a nitrogen containing buffering material in an amount such that the ratio of nitrogen containing material to aluminum is the range of 0.05-0.26:1, and which nitrogen containing material is selected from the group consisting of a nitrogen containing buffering material of formula

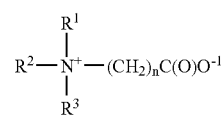

where n is a number in the range of 1-20, and each of $R^1$, $R^2$, and $R^3$ is independently selected from the group consisting of hydrogen, methyl and ethyl; and (c) the salt has a pH in the range of 2-4 at a concentration of 15%; wherein the salt is free of any other halide scavenging material and has a value of at least 0.50 for the ratio calculated as:
area of Peak 5/total area under Peak 2+Peak 3+Peak 4+Peak 5.

11 Claims, No Drawings

HIGH EFFICACY, LOW IRRITATION ALUMINUM SALTS AND RELATED PRODUCTS

CROSS-REFERENCE TO RELATED APPLICATIONS

This application is a continuation of U.S. application Ser. No. 10/314,712, filed Dec. 9, 2002, now abandoned the disclosure of which is hereby incorporated herein by reference in its entirety.

FIELD OF THE INVENTION

This invention relates to a class of high efficacy, low irritation aluminum salts that may be used to formulate non-aerosol, propellant-free antiperspirants and/or deodorants.

BACKGROUND OF THE INVENTION

A variety of art is available that describes various salts and methods of making them.

U.S. Pat. No. 4,331,609 to Orr teaches an antiperspirant active comprising aluminum and zirconium made with separate aluminum and zirconium compounds as well as a neutral amino acid wherein the molar ratio of neutral amino acid to total metal is from about 0.90 to about 0.24. The total metal:chlorine ratio in the complex that is formed is less than 1.30.

U.S. Pat. No. 4,499,069 to Krafton describes a stable antiperspirant emulsion comprising an aluminum salt, volatile cyclic silicone, water, and a low pH-stable emulsifier mixture of polyethylene glycol (21) stearyl ether and a lipophilic co-emulsifier such that the HLB of the emulsifier mixture is greater than 7.5 and less than 9.9.

U.S. Pat. No. 4,675,177 to Geary teaches aluminum salts comprising particular lactate, citrate, tartrate or adipate esters for enhanced efficacy.

U.S. Pat. No. 4,871,525 to Giovanniello et al describes a solid powder of aluminum zirconium hydroxyl halide glycinate complex having improved antiperspirant activity wherein the glycine is used to prevent gel formation. The ratio of Zr to glycine is less than 1:1.

U.S. Pat. No. 5,234,677 to Murray et al teaches a method for making enhanced aluminum chlorides with increased efficacy.

U.S. Pat. No. 5,384,117 to Vu et al teaches a substantially clear anhydrous antiperspirant compositions that can me made with an aluminum chlorohydrate salt in solid particulate form suspended in an essentially anhydrous vehicle, wherein the salt is free of opacifying contaminants and the salt and vehicle have refractive indices in selective ranges.

U.S. Pat. No. 5,393,518 to Kwass teaches a stable and substantially clear antiperspirant composition comprising a stable water-in-oil emulsion, wherein the oil phase is at lest 30% of ht e product.

U.S. Pat. No. 5,356,612 to Curtin, et al describes an antiperspirant comprising a basic aluminum salt mixed with monosilicic acid in aqueous solution.

U.S. Pat. Nos. 5,718,876 and 5,908,616 to Parekh describes a method for making enhanced aluminum halides with increased efficacy.

U.S. Pat. No. 5,599,533 to Stepniewski et al describes a stable water-in-oil emulsion system formed of an organopolysiloxane elastomer, a vehicle in which the elastomer is dispersed or dispersible, a stabilizing agent (such as a selected electrolyte), a surfactant and an aqueous component and a process for forming the stable water-in-oil emulsion. Possible choices for electrolytes are alkali metal salts and alkaline earth salts, as well as aluminum chlorohydrate, and polyelectrolytes. When the stabilizing agent is, or includes, an electrolyte, it amounts to about 0.1 to 5 wt.-% and more preferably 0.5 to 3 wt. % of the total composition.

U.S. Pat. No. 6,024,945 to Parekh describes aerosol products comprising an aluminum salt, 1,1-difluoroethane in combinations with selected additives to prevent the formation of toxic compounds. These additives include, for example, and an amino acid (such as glycine) selected salts thereof, or metal glycinates.

U.S. Pat. No. 6,066,314 to Tang describes the use of post added glycine to aluminum zirconium salts in an amount in the range of 1:1.2-1:5 of zirconium:amino acid on a weight:weight basis.

U.S. Pat. No. 6,126,928 to Swaile describes antiperspirant compositions wherein the molar ratio of neutral amino acid to total metal (aluminum+zirconium) is from about 0.90 to about 0.24, and the mole ratio of (aluminum+zirconium):chlorine is less than about 1.30:1.

EP publication number 0 047 650 describes aqueous solution-stable antiperspirant complexes comprising an aluminum compound, a zirconium or hafnium compound, a water soluble neutral amino acid and an inorganic acid. The molar ratio of neutral amino acid to total metal is from about 0.90 to about 0.24 in an aqueous system, and the molar ratio of neutral amino acid to total metal is from about 0.90 to about 0.75 in a non-aqueous system. The total metal:chlorine ratio in the complex that is formed is less than 1.30.

United Kingdom Patent Application GB 2,076,289 describes an antiperspirant compositions comprising a combination of an aluminum chloride and an aluminum zirconium hydroxychloride in a synergistic mixture. The metal:chloride ratio is less than 0.9.

Canadian Patent 1,153,313 describes an antiperspirant composition which contains a buffering agent such as glycine with a synergistic mixture of aluminum chlorohydrate, aluminum chloride or aluminum zirconium polychlorohydrate complex. The molar ratio of aluminum to chloride is in the range of 0.78:1 to abut 1.95:1. Various salts are described which have a metal:halide ratio of 2.1:1-0.9:1. The glycine:zirconium ratio is much less than 1:1.

None of the above cases described the combination of metal to chloride in combination with the glycine to zirconium ratio as found in the instant invention. Thus, it is surprising that the antiperspirant actives described in this invention provide more efficacious cosmetic products.

While a great deal of work has been done on Al/Zr salts, there is still a need to have aluminum salts to use in a variety of products (including non-aerosol sprays for antiperspirants and/or deodorants where zirconium cannot be used) that are capable of being formulated into products with reduced irritation and better fragrance stability.

BRIEF SUMMARY OF THE INVENTION

This invention comprises zirconium-free aluminum salts which:
(a) have an aluminum to chloride molar ratio in the range of 0.5-2.5:1;
(b) comprises a nitrogen containing buffering material (particularly glycine) in an amount such that the ratio of nitrogen containing material to aluminum is the range of 0.05-0.26:1 and preferably in the range of 0.05-0.16:1 and which nitrogen containing material is selected from the group consisting of a nitrogen containing a buffering material of formula

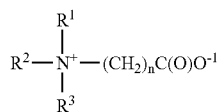

where n is a number in the range of 1-20, and each of $R^1$, $R^2$, and $R^3$ is independently selected from the group consisting of hydrogen, methyl and ethyl (preferably methyl); and (c) the salt has a pH in the range of 2-4 (when measured in water at a concentration of 15%);

wherein the salt is free of any other halide scavenging material and has a value of at least 0.50 for the ratio calculated as:

$$\frac{\text{area of Peak 5}}{\text{total area under Peak 2 + Peak 3 + Peak 4 + Peak 5}}$$

The salts of the invention may be made as spray dried powders or made as solutions of up to 50 weight % based on the weight of the final product.

The invention also includes antiperspirant and/or deodorant products made with these salts. Such formulations may be made as sticks, soft solids or creams, roll-ons or non-aerosol sprays. The formulations are free of propellants.

This invention is limited to aluminum antiperspirant salts that do not contain zirconium.

DETAILED DESCRIPTION OF THE INVENTION

It has been found that by adding a selected amount of a nitrogen containing buffering agent (for example, glycine, alanine, serine, glutamine, threonine, valine, leucine, betaine) and lowering the aluminum:chloride ratio in aluminum chlorohydroxide salts, the amount of smaller aluminum species is increased with an appropriate increase in efficacy. Since the pH of such salts with lowered aluminum: chloride ratio is low, the problems of irritancy, fragrance compatibility, color changes, etc. must be addressed. It has been found that by adding a nitrogen containing compound as described above, the pH may be elevated to an acceptable range while still maintaining or increasing the relative amount of the smallest Peak 5 aluminum species in solution. It is also critical to note, however, that the use of too high an amount of the nitrogen buffering material may cause new problems such as unwanted gellation of the active (with corresponding decrease in efficacy). Thus, it has been found that in solutions of the salts, the amount of nitrogen buffering material must be kept below 5 weight % (and preferably less than 3%) to achieve a stability of 2 weeks at room temperature for an anhydrous aluminum dichlorohydrate in a water solution at an anhydrous level of 25% active salt without water. Another way of describing the amount of nitrogen containing material that may be used is by specifying a ratio range. In particular, the molar ratio of the nitrogen containing material (particularly glycine) to aluminum should be in the range of 0.05-0.26:1 and preferably in the range of 0.05-0.16:1. The lower concentrations may be used for longer stability times such as 3 weight % for 4 weeks and 2 weight % for several months. Of course the salt may be spray dried to create a material with much longer stability such as on the order of years. The dried salt material may then be added to the formulation during the manufacturing process. Thus, efficacy may be maintained in aluminum only systems.

The salts of this invention may be made in a variety of ways:

Method A: An aluminum dichlorohydrate (ADCH) solution of ADCH salt in water of suitable concentration is mixed with a suitable concentration of a powdered form of the nitrogen containing material such as glycine. The mixture is stirred at room temperature to obtain the product. Aluminum sesquichlorohydrate (ASCH may be substituted for ADCH.

Method B: Method A is repeated and the product is then spray dried to obtain the salt in powder form.

If the product is used as a solid powder, the size of the particles of antiperspirant active of the invention currently does not appear to be critical and may include conventional sizes such as greater than 2 to 100 microns, with selected grades having an average particle size of 30-40 microns; finer sized grades having an average particle size distribution from 2-10 microns with average size of about 7 microns as made by a dry-grinding method; and micronized grades of the type described in a co-pending patent application PCT case WO 01/97,768 having an average particle size of less than or equal to 2 microns, particularly less than or equal to 1.5 microns.

The enhanced salts of this invention may be used to formulate antiperspirants having improved efficacy. Such antiperspirants include solids such as sticks and creams (creams sometimes being included in the term "soft solid"), gels, liquids (such as are suitable for roll-on products), and aerosols. The forms of these products may be suspensions or emulsions.

It is preferred that the glycol content of the formulations be kept to a minimum, preferably not exceeding 1.0 weight %.

Examples of suitable formulations include the following.

Sticks—Stick products may be made with conventional gelling agents such as stearyl alcohol and dibenzylidene sorbitol. A sample formulation is as follows:

40-55% (particularly 45%) cyclomethicone (particularly D4-D6 and especially D5 cyclomethicone)
20-30% (particularly 21%) stearyl alcohol
7-15% (particularly 10%) talc
15-22% (particularly 22%) aluminum antiperspirant active in powder form
1-3% (particularly 2%) fragrance (optional)

Roll-Ons—
45-65% (particularly 55%) cyclomethicone (particularly D4-D6 and especially D5 cyclomethicone)
0.1-10% (particularly 3%) cyclomethicone/dimethicone copolyol (such as Dow Corning 2-5185 C)
10-25% (particularly 20%) antiperspirant active in solution form (25-45% actives on an anhydrous basis in water)
5-30% (particularly 20%) water
1-3% (particularly 2%) fragrance (optional)

Soft solids—Soft solids may be made with formulations described in co-pending patent application (U.S. Ser. No. 9/273,152 and PCT Publication number WO 99/51192 A sample formulation is as follows:
40-70% (particularly 50%) elastomer in cyclomethicone (KSG-15 from Shin-Etsu)

5-15% (particularly 6%) polyethylene (for example, beads having a density in the range of 0.91-0.98 g/cm$^3$ and an average particle size in the range of 5-40 microns)

10-20% (particularly 15%) C12-15 alkylbenzoate (FINSOLV TN from Finetex)

0.1-25%% (particularly 22%) antiperspirant active in powder form 1-15% (particularly 5%) dimethicone (100 centistokes)

1-3% (particularly 2%) fragrance (optional)

Gels—Gels may be made with a variety of formulations such as 5-50% (particularly 29%) cyclomethicone (particularly D4-D6 and particularly D5)

0.1-10% (particularly 3%) cyclomethicone/dimethicone copolyol (such as Dow Corning 2-5185 C)

0-10% (particularly 5%) hydrogenated polyisobutene 250

0-10% (particularly 5%) C12-15 alkylbenzoate (FINSOLV TN from Finetex)

0-10% (particularly 5%) dimethicone (100 centistokes)

0.1-25% (particularly 20%) antiperspirant active in powder form or 10-25% (particularly 20%) of active in solution (25-45% actives on an anhydrous basis)

5-50% (particularly 30%) water 1-3% (particularly 2%) fragrance (optional)

Note that in the explanation of the invention, where water is listed it is intended to count the contribution of the water present in the antiperspirant solution as part of the overall water content. Thus, water is sometimes listed as part of the actives solution or sometimes listed separately.

In a preferred embodiment the refractive indices of the external and internal phases are matched within 0.005 to obtain a clear product.

Particular formulations of interest include:

Formulation A:

0.5-2.5% dimethicone copolyol (for example, Dow Corning 2-5185C (48%))

55-65% elastomer in cyclomethicone (for example, DC-9040 from Dow Corning Corporation (Midland, Mich.) or KSG-15 from Shin-Etsu Silicones of America (Akron, Ohio))

1-10% PPG-3 myristyl ether 10-25% antiperspirant active of the invention 10-25% water 0.5-1.5% fragrance Formulation B 1.0-3.0% dimethicone copolyol (for example, Dow Corning 2-5185C (48%))

40-60% elastomer in cyclomethicone (for example, DC-9040 from Dow Corning Corporation (Midland, Mich.) or KSG-15 from Shin-Etsu Silicones of America (Akron, Ohio))

1-5% cyclomethicone (in addition to that found in the elastomer)

4-12% PPG-3 myristyl ether 15-30% antiperspirant active of the invention 15-35% water 0.5-1.5% fragrance Formulation C 1.0-3.0% dimethicone copolyol (for example, Dow Corning 2-5185C (48%))

1-10% hydrogenated polyisobutene (for example, Fancol™ Polyiso 250)

40-55% elastomer in cyclomethicone (for example, DC-9040 from Dow Corning Corporation (Midland, Mich.) or KSG-15 from Shin-Etsu Silicones of America (Akron, Ohio))

3-8% PPG-3 myristyl ether 15-20% antiperspirant active of the invention 20-30% water 1.0-3.0% fragrance Formulation D 1.0-3.0% dimethicone copolyol (for example, Dow Corning 2-5185C (48%))

40-60% elastomer in cyclomethicone (for example, DC-9040 from Dow Corning Corporation (Midland, Mich.) or KSG-15 from Shin-Etsu Silicones of America (Akron, Ohio))

3-8% PPG-3 myristyl ether 15-30% antiperspirant active of the invention 15-30% water 0.5-1.5% fragrance 1-10% diethylhexyl naphthalate Formulation E 0.5-2.5% dimethicone copolyol (for example, Dow Corning 2-5185C (48%))

60-70% elastomer in cyclomethicone (for example, DC-9040 from Dow Corning Corporation (Midland, Mich.) or KSG-15 from Shin-Etsu Silicones of America (Akron, Ohio))

7-10% antiperspirant active of the invention 25-35% water 1-10% methylpropylene diol (MP Diol)

0.5-1.5% fragrance

Formulation F 1.0-3.0% dimethicone copolyol (for example, Dow Corning 2-5185C (48%))

6-10% hydrogenated polyisobutene (for example, Fancol™ Polyiso 250)

35-45% elastomer in cyclomethicone (for example, DC-9040 from Dow Corning Corporation (Midland, Mich.) or KSG-15 from Shin-Etsu Silicones of America (Akron, Ohio))

6-10% PPG-3 myristyl ether 40-50% antiperspirant active of the invention as 43% active in water no additional water 0.5-1.0% fragrance Formulation G 0.1-0.6% dimethicone copolyol (for example, Dow Corning 2-5185C (48%))

4-7% hydrogenated polyisobutene (for example, Fancol™ Polyiso 250)

40-50% elastomer in cyclomethicone (for example, DC-9040 from Dow Corning Corporation (Midland, Mich.) or KSG-15 from Shin-Etsu Silicones of America (Akron, Ohio))

4-7% PPG-3 myristyl ether 40-50% antiperspirant active of the invention as 43% active in water no additional water 0.5-1.0% fragrance Formulation H 0.5-2.0% dimethicone copolyol (for example, Dow Corning 2-5185C (48%))

1-7% hydrogenated polyisobutene (for example, Fancol™ Polyiso 250)

40-50% elastomer in cyclomethicone (for example, DC-9040 from Dow Corning Corporation (Midland, Mich.) or KSG-15 from Shin-Etsu Silicones of America (Akron, Ohio))
45-55% antiperspirant active as 43% active of the invention in water
no additional water
0.5-1.5% fragrance Formulation I
2-7% dimethicone copolyol (for example, Dow Corning 2-5185C (48%))
0.1-1% Oleath-20
1-5% C12-15 alkyl benzoate (FINSOLV TN)
15-25% elastomer in cyclomethicone (for example, DC-9040 from Dow Corning Corporation (Midland, Mich.) or KSG-15 from Shin-Etsu Silicones of America (Akron, Ohio))
15-25% antiperspirant active
15-30% water
0.5-1.5% fragrance The cosmetic composition according to the present invention can be packaged in conventional containers, using conventional techniques. Where a gel, cream or soft-solid cosmetic composition is produced, the composition can be introduced into a dispensing package (for example, conventional packages for gels with glide on applicators, jars where the gel or cream is applied by hand, and newer style packages having a top surface with pores) as conventionally done in the art. Thereafter, the product can be dispensed from the dispensing package as conventionally done in the art, to deposit the active material, for example, on the skin. For sticks, sprays, aerosols and roll-ons the compositions can be placed in a conventional types of container (with the inclusion of propellants in aerosols). This provides good deposition of the active material on the skin.

Compositions of the present invention can be formulated as clear, translucent or opaque products, although clear products are preferred. A desired feature of the present invention is that a clear, or transparent, cosmetic composition, (for example, a clear or transparent deodorant or antiperspirant composition) can be provided. The term clear or transparent according to the present invention is intended to connote its usual dictionary definition; thus, a clear liquid or gel antiperspirant composition of the present invention allows ready viewing of objects behind it. By contrast, a translucent composition, although allowing light to pass through, causes the light to be scattered so that it will be impossible to see clearly objects behind the translucent composition. An opaque composition does not allow light to pass therethrough. Within the context of the present invention, a gel or stick is deemed to be transparent or clear if the maximum transmittance of light of any wavelength in the range 400-800 nm through a sample 1 cm thick is at least 35%, preferably at least 50%. The gel or liquid is deemed translucent if the maximum transmittance of such light through the sample is between 2% and less than 35%. A gel or liquid is deemed opaque if the maximum transmittance of light is less than 2%. The transmittance can be measured by placing a sample of the aforementioned thickness into a light beam of a spectrophotometer whose working range includes the visible spectrum, such as a Bausch & Lomb Spectronic 88 Spectrophotometer. As to this definition of clear, see European Patent Application Publication No. 291,334 A2. Thus, according to the present invention, there are differences between transparent (clear), translucent and opaque compositions.

It is believed that the more homogeneous the composition is and the more uniform the particle size, the better properties of the composition.

Throughout the present specification, where compositions are described as including or comprising specific components or materials, or where methods are described as including or comprising specific steps, it is contemplated by the inventors that the compositions of the present invention also consist essentially of, or consist of, the recited components or materials, and also consist essentially of, or consist of, the recited steps. Accordingly, throughout the present disclosure any described composition of the present invention can consist essentially of, or consist of, the recited components or materials, and any described method of the present invention can consist essentially of, or consist of, the recited steps.

EXAMPLES

The following Examples are offered as illustrative of the invention and are not to be construed as limitations thereon. In the Examples and elsewhere in the description of the invention, chemical symbols and terminology have their usual and customary meanings. In the Examples as elsewhere in this application values for n, m, etc. in formulas, molecular weights and degree of ethoxylation or propoxylation are averages. Temperatures are in degrees C. unless otherwise indicated. If alcohol is used, it is 95% unless otherwise indicated. Unless otherwise indicated, "water" or "D.I. water" means deionized water. As is true throughout the application, the amounts of the components are in weight percents based on the standard described; if no other standard is described then the total weight of the composition is to be inferred. Various names of chemical components include those listed in the *CTFA International Cosmetic Ingredient Dictionary* (Cosmetics, Toiletry and Fragrance Association, Inc., $7^{th}$ ed. 1997). While specific amounts of particular elastomers have been described, there are chemical differences in the variety of elastomers that are available. The use of different elastomers may result in the need to increase or decrease the amount of elastomer used in a particular formulation, especially if a clear product is desired.

In the Examples, as elsewhere in the description of the invention, reference is made to using the antiperspirant active either as a powder or in some type of solution such as dissolved in water at a concentration or 25-45% actives on an anhydrous basis.

Examples 1-4

Antiperspirant Salts

Improved aluminum di-chlorohydrate salts (10.0% anhydrous) can be made with glycine as follows using the amounts of ingredients listed in Table A. Glycine powder (at the level listed in Table A) and distilled water are added into an aluminum dichlorohydrate solution (Westchlor 100, 38% anhydrous excluding waters of hydration) and stirred for 5 minutes to make six Examples as shown in Table A. The concentration for all the Examples 1-6 is 10% by weight. Table A also contains the pH values as measured with a Corning pH meter 430. Finally, a profile was run on each of the solutions listed in Table A and the areas under each peak were calculated. The method used is the same one described in U.S. Pat. No. 6,066,314. The Size exclusion chromatography ("SEC") column separates the species by molecular size, using a refractive index (RI) detector connected to the column outlet. The % of each peak of the whole was also calculated and the values are listed in Table A. All concentrations are in % by weight based on the entire weight of the solution. The increase in Peak 5 species is supportive of improved efficacy. (Also see U.S. Pat. No. 6,375,937.)

Size exclusion chromatography method is frequently used for obtaining information on polymer distribution in antiperspirant salt solutions. With appropriate chromatographic columns, at least 5 distinctive groups of polymer species can be detected in an aluminum salt, appearing in a chromatogram as peaks 1, 2, 3, 4, and a peak referred to here as "5". Peaks 2 and 3 are larger aluminum species. Peak 4 is smaller aluminum species (aluminum oligomers) and has been correlated with enhanced efficacy for ACH salts. Peak 5 is the smallest aluminum species. The relative retention time ("Kd") for each of these peaks varies depending on the experimental conditions. Data for Table A was obtained using the SEC method described in an issued patent owned by the same company as this case, U.S. Pat. No. 6,066,314, incorporated by reference as to the test method described therein.

TABLE A

| Example | Concentration of glycine (anhydrous) | pH | % Peak 3 | % Peak 4 | % Peak 5 |
|---|---|---|---|---|---|
| 1 | 0 | 2.67 | 24.58 | 25.61 | 49.81 |
| 2 | 1 | 2.79 | 19.93 | 17.15 | 62.92 |
| 3 | 2 | 2.84 | 18.85 | 13.85 | 67.30 |
| 4 | 3 | 2.94 | 18.75 | 13.92 | 67.34 |
| 5 | 4 | 3.10 | 17.87 | 14.31 | 67.81 |
| 6 | 5 | 3.50 | 18.01 | 14.63 | 67.36 |

Examples 7-12

Analytical Data

Using the concentration listed in Table B, betaine powder and distilled water are added into an aluminum dichlorohydrate solution (Westchlor 100, 48% anhydrous) and stirred for five minutes to make Examples 7-12 with a concentration of 10 weight % ADCH. The same analytical method described for Examples 1-6 was used to obtain the data listed in Table B.

TABLE B

| Example | Concentration of betaine (anhydrous) | pH | % Peak 3 | % Peak 4 | % Peak 5 |
|---|---|---|---|---|---|
| 7 | 0 | 2.67 | 24.58 | 25.61 | 49.81 |
| 8 | 1 | 2.72 | 24.10 | 23.63 | 52.27 |
| 9 | 2 | 2.80 | 22.76 | 22.7 | 54.54 |
| 10 | 3 | 2.82 | 20.83 | 21.37 | 57.80 |
| 11 | 4 | 2.90 | 20.83 | 21.37 | 57.80 |
| 12 | 5 | 3.03 | 18.20 | 18.33 | 63.47 |

Examples 13-18

Efficacy Screening

A clinical evaluation with forearm screening using the procedure described below was done with liquid gel formulae containing antiperspirant salt solution made with aluminum dichlorohydrate, water and glycine so that the concentration of the antiperspirant on an anhydrous basis is 25 weight % and the concentration of glycine is the amount listed in Table C. It will be noted that the % sweat reduction of the salt in stored solution (8 days at about 40 degrees C. (105 degrees F.) decreases after the amount of glycine exceeds 3%. The sweat reduction for the Examples with 1% and 2% glycine is similar to the one without glycine. This means that the use of glycine does not negatively impact efficacy. The drop in efficacy at the addition levels of 3% and 5% glycine is due to the gellation of the aluminum salt in the internal phase. Thus, if a solution of the salt is to be used, the concentration should be kept less than 3%. Table C shows that the use of a 1% or 2% salt material of the invention as a solution to achieve the low irritancy and fragrance favorable properties in a clear, non-yellowing solution can be done without sacrificing efficacy. Note that spray drying the salt product can keep this gellation from happening and allow the use of higher concentrations of glycine.

TABLE C

| Example | Concentration of glycine | Forearm rating (% sweat reduction) |
|---|---|---|
| 13 | 0% | 60% |
| 14 | 1% | 70% |
| 15 | 2% | 60% |
| 16 | 3% | 25% |
| 17 | 4% | NA |
| 18 | 5% | 15% |

Examples 19-36

Powder Forms

Each of the Examples 1-18 can be formed into a powder using conventional spray drying or freeze drying techniques known to those skilled in the art. Examples of such methods may be found in U.S. Pat. No. 5,589,196. Note that in spray drying the material, the maximum amount of water left in the spray dried product should not exceed 25 weight %.

Example 37

General Method for Making Antiperspirant Products

In general, the external and internal phases are formed separately either at room temperature or with heating as described below. The internal phase is added to the external phase very slowly while stirring at to form an emulsion. After the addition has been completed, the mixture is stirred at higher speed to achieve a homogeneous mixture. The final formula viscosity is then achieved by homogenizing the emulsion under either batch or continuous process conditions as described below. The fragrance may be added at any time during the process prior to final homogenization.

Preparation of the External Phase:

The ingredients to be used in the external phase (including the elastomer) are weighed out at room temperature and combined in a suitable vessel such as a 2 liter glass beaker. The mixture is stirred at about 500 rpm for 15-20 minutes using an overhead mixer such as a Lightnin Mixer Model L1003. If a waxy or solid emollient is to be added to the external (also called "continuous") phase, the mixture may be heated to facilitate dissolution while stirring then cooled to room temperature prior to combination with the internal phase as described below. The elastomer component is obtained as a suspension of elastomer in cyclomethicone (for example at a concentration of 6% active in D5 cyclomethicone). The elastomer component is added to the external phase with stirring at high speed (500-700 rpm for a 0.5 kilogram batch) until no particles of elastomer are visible to the eye.

Preparation of the Internal Phase:

The internal dispersed phase is prepared as described below. Ingredients are mixed for a time sufficient to achieve homogeneity. The antiperspirant active used is weighed into a large beaker equipped with an overhead stirrer. Other internal phase ingredients are then added while stirring.

The fragrance (if any is used) is added last and may be added either to the internal phase or the external phase or the final formula prior to homogenization. For many of the examples described here, one could add the fragrance to the internal phase.

If an optional non-ionic emulsifier such as Oleath-20 is used, the emulsifier and propylene glycol are combined in a separate beaker and heated to 40 degrees C. with stirring until the non-ionic emulsifier completely dissolved. The heat is turned off and the remaining ingredients to be used in the internal phase, including the antiperspirant active are weighed out and added to the mixture of propylene glycol and non-ionic emulsifier.

If water or a salt solution are used, the internal phase is prepared as follows. The solution containing antiperspirant active salt as received from supplier is weighed into a large beaker equipped with a magnetic stirrer. Additional ingredients such as propylene glycol, ethanol and water are added while stirring. If a salt water solution is used (such as for NaCl, etc.), the salt water solution is prepared by dissolving the crystalline salt in water in a separate beaker and stirring until dissolved. The salt water solution is then added to the rest of the internal phase and the mixture is stirred until homogeneous.

Preparation of the Emulsion:

The internal phase made as described above is then added to the external phase over the course of 15-30 minutes while stirring at a speed of 500-700 rpm. After the addition is complete, the mixture is stirred at 500-700 rpm for 20 minutes using a Lightnin Mixer Model L1003. The mixture is then homogenized for 2-4 minutes (especially 3 minutes) using a homogenizer from Greerco Corp., Hudson, N.H. at a reading of about 60 on a Powerstat Variable Autotransformer from Superior Electric Co., Bristol, Conn.

Further Processing:

The product is then further processed by homogenization to achieve the desired final viscosity. This can be done by using a Gilford-Wood Model 1-L (Greerco Corp., Hudson, N.H.) homogenizer. The homogenizer speed is controlled by a Powerstat Variable Autotransformer Type 3PN116B (Superior Electronic. Co., Bristol, Conn.). Typical voltage setting and processing time are chosen to give a desired final formula viscosity.

An other method of homogenization of the final product is to pass the emulsion through a colloid mill such as a Sonic Tri-Homo Colloid Mill or a process sonolator such Sonic Production Sonolator 200-30 both available from Sonic Corporation of Stratford, Conn. Process conditions are chosen to give the desired final product viscosity.

Examples 38-58

Compositions

The method described in Example 37 may be used to make the compositions listed in Tables D and E with the types and amounts of ingredients listed in the Tables. Amounts are in percent by weight based on the total weight of the composition. For the antiperspirant active, any of the solutions of actives described in Examples 1-18 may be used.

TABLE D

| Ingredient | Ex. 38 | Ex. 39 | Ex. 40 | Ex. 41 | Ex. 42 | Ex. 43 | Ex. 44 | Ex. 45 | Ex. 46 | Ex. 47 |
|---|---|---|---|---|---|---|---|---|---|---|
| External Phase | | | | | | | | | | |
| Elastomer (KSG-15, 6% active) | 62 | 50 | 48 | 40 | 41.5 | 42.0 | 46.5 | 35 | 32.17 | 25 |
| Dimethicone copolyol (Dow Corning 2-5185, 48% active in cyclomethicone) | 2 | 2 | 1.5 | 4 | 1.5 | 0.5 | 1.0 | 1.0 | 2.48 | 1.0 |
| Hydrogenated polyisobutene (Polyiso 250) | 0 | 0 | 5 | 8 | 5 | 5 | 5 | 5 | 4.95 | 0 |
| PPG-3 Myristyl Ether | 5 | 5 | 4.5 | 0 | 4.5 | 5.0 | 0 | 0 | 0 | 5 |
| C12–15 alkyl benzoate (FINSOLV TN) | 0 | 0 | 0 | 2.0 | 0 | 0 | 0 | 0 | 0 | 0 |
| Cyclomethicone (Dow Corning 245) | 0 | 2 | 0 | 0 | 0 | 0 | 0 | 0 | 0 | 0 |
| Fragrance | 1 | 1 | 1 | 1 | 1 | 1 | 1 | 1 | 1 | 0 |
| Internal Phase | | | | | | | | | | 0 |
| Antiperspirant Active[a] | 15 | 20 | 17.5 | 19.5 | 46.5 | 46.5 | 46.5 | 58 | 59.40 | 48.45 |
| Water (deionized)[b] | 15 | 20 | 22.5 | 25 | 0 | 0 | 0 | 0 | 0 | 0 |
| Oleath-20 (HLB > 8) | 0 | 0 | 0 | 0.5 | 0 | 0 | 0 | 0 | 0 | 19.55 |
| Total | 100 | 100 | 100 | 100 | 100 | 100 | 100 | 100 | 100 | 100 |

[a]= Any of the actives described in Examples 1–18 may be used.
[b]= Note that in the examples, sometimes the antiperspirant active is listed as a solution (which will include a water component) under the "active" designation with little or no water and sometimes the active and water are listed separately.

TABLE E

| Ingredient | Ex. 48 | Ex. 49 | Ex. 50 | Ex. 51 | Ex. 52 | Ex. 53 | Ex. 54 | Ex. 55 | Ex. 56 | Ex. 57 | Ex. 58 |
|---|---|---|---|---|---|---|---|---|---|---|---|
| External Phase | | | | | | | | | | | |
| Elastomer (DC 9040) 12% active) | 55 | 62 | 62 | 40 | 41.5 | 25 | 31.5 | 21 | 17 | 17 | 50 |
| Dimethicone copolyol (Dow Corning 2-5185, 48% active in cyclomethicone) | 1 | 2 | 2 | 4 | 1 | 1 | 2.5 | 1 | 1 | 1 | 2 |
| Hydrogenated polyisobutene (Polyiso 250) | 5 | — | — | 8 | 5 | — | 5 | 1.5 | 1.5 | 1.5 | — |
| PPG-3 Myristyl Ether | 3 | 4.5 | 5 | — | 5 | 5 | — | 0.5 | 0.5 | 0.5 | 5.0 |
| C12–15 alkyl benzoate (FINSOLV TN) | — | — | — | 2 | — | — | — | — | — | — | — |
| Cyclomethicone (Dow Corning 245) | — | — | — | — | — | — | — | 5 | 9.0 | 9.0 | 2.0 |
| Fragrance | 1 | 1 | 1 | 1 | 1 | 1 | 1 | 1 | 1 | 1 | 1 |
| Internal Phase | | | | | | | | | | | |
| Antiperspirant Active[a] | 15 | 15.5 | 30 | 19.5 | 46.5 | 48.45 | 60.0 | 60.5 | 63.68 | 60.13 | 20 |
| Water (deionized)[b] | 20 | 15 | | 25 | | 19.55 | | 9.5 | 6.32 | 9.87 | 20 |
| Oleath-20 (HLB > 8) | — | — | — | 0.5 | — | — | — | — | — | — | — |
| Total | 100 | 100 | 100 | 100 | 100 | 100 | 100 | 100 | 100 | 100 | 100 |

[a] = See explanation of actives used. Actives according to Examples 1–18 may be used.
[b] = Note that in the examples, sometimes the antiperspirant active is listed as a solution (which will include a water component) under the "active" designation with little or no water and sometimes the active and water are listed separately.

Example 59

Forearm Test

A forearm starch/iodine test may be used as a rapid screening tool for underarm formulations prior to underarm clinical testing. The following procedure may be used for all tests discussed in this patent document. Panelists should be chosen who had not placed any antiperspirant products on their interior forearms for at least 14 days prior to the start of the test. Test formulations are applied on the inner forearms in preselected amounts. A control product such as a commercial product (Lady Speed Stick AP) is applied to one site on the panelists' arms as a positive control. After application of the formulations, the sites are occluded with covering chambers for one hour under conditions of about 40 degrees C. and 30% relative humidity. Panelists then remove the covering chambers. One hour after removal of the covering chambers, the forearms are each washed with a mild soap. This is repeated for the first two days of the study. On the third day of product application, the sites are occluded for one (1) hour, but are not washed with soap. The panelists perform their normal cleansing regimen using a mild soap during the course of the study. Approximately 20 hours after the last application of the products, the panelists are equilibrated in a room at 40 degrees C. (105° F.) and 40% relative humidity for 15 minutes. The panelists arms are then patted dry with a paper towel followed by application of paper strips impregnated with iodine to the test sites. Exposure to sweat causes the paper to turn purple at sites of hydration, generating a spatial map of the firing sweat glands. The papers are removed once the purple spots begin to appear on the backside or after five minutes, whichever comes first. Images of the papers may be digitized to quantify the amount of purple spot coverage. Once images are digitized, the area for measurement is identified using the same area as occluded by the chambers. A comparison of the total area of hydration for treated skin versus untreated sites is used to calculate a % Sweat Reduction (Eq: 1). The area of sweat from untreated sites used in Equation 1 is calculated as the mean sweat areas of all the untreated sites directly adjacent to the treated site of interest. Since the number of firing sweat glands varies along the surface of the volar forearm, the mean sweat area of the adjacent untreated sites is used to approximate the area of sweat which would have been produced if a formula had not been applied to the treatment site.

$$\% \text{ Sweat Reduction} = 100[1-(\text{Area-Treated}/\text{Mean}(\text{Area-Untreated}))] \quad \text{Eq: 1}$$

Example 60

Soft Solid with Powdered Salt

An antiperspirant product can be made using the following ingredients:

Part 1

51% Cyclomethicone (D5); 3% PPG-3 myristyl ether; 6% C12-15 alkyl benzoate (FINSOLV TN from Finetex Inc., Elmwood Park, N.J.); 1% fragrance; 10% vinyl polydimethyl siloxane elastomer 10% in D5 cyclomethicone (USG-103 from Shin-Etsu Silicones of America, Inc., Akron, Ohio);

Part 2

5% fumed silica (Cab-O-Sil from Cabot Corp.); 24% of an active made as for Example 32

All ingredients in Part 1 are added into a beaker, and stirred at about 400 rpm using an overhead mixer such as a Lightnin' Mixer Model L1003 until it becomes visually homogeneous. The mixture is then transferred into the container of a Hobart Mixer (Model N-50), where the ingredients in Part 2 have been placed. The Hobart Mixer is then turned on and running at "low" speed for 30 minutes or until a uniform creamy product is formed.

Example 61

Stick with Powdered Salt

An antiperspirant product can be made using the following ingredients:

Part 1
10% Cyclomethicone (DC 345 from Dow Corning); 20% stearyl alcohol; 12% C12-15 alkyl benzoate (FINSOLV TN); 4% hydrogenated castor oil (MP80); 4% PEG-8 distearate Part 2
20.80% Cyclomethicone (DC 345); 3% dimethicone copolyol (DC 5225C from Dow Corning, 10%); 25% of an active as described in Example 33

Part 3
1% fragrance

Formation of Part 1
Mix cyclomethicone and FINSOLV TN at 300 rpm using an overhead mixer such as a Lightnin' Mixer Model L1003. Heat the mixture to 70° C. and add stearyl alcohol with continuous stirring. After stearyl alcohol is melted, the temperature is increased to 75° C. Melt PEG-8 distearate by adding it to the mixture. Increase temperature further to 80° C. Add hydrogenated castor oil. Stir it in the solution until it is dissolved.

Formation of Part 2
Put all ingredients in Part 2 in a separate beaker. Heat it to 70° C. with stirring.

Formation of Stick
Add Part 2 to Part 1 at 70-75° C., and mix at 450 rpm for 15 min. Turn the heater off and let it cool to 65° C., and add fragrance. Pour the sample out into barrels at 58° C. Form sticks by placing the barrels into refrigerator for 15 minutes.

Example 62

Roll-On with ADCH Solution

An antiperspirant product can be made using the following ingredients:

Part 1
3% dimethicone copolyol (DC 5225C); 13.5% dimethicone (2 cst viscosity, DC 200 from Dow Corning); 2.5% PPG-3 myristyl ether; 0.80% fragrance Part 2
72% of the composition described in Example 14; 8.2% propylene glycol Mix the ingredients in Part 1 to form a clear solution with an overhead mixture. Mix the ingredients in Part 2 in a separate beaker to form an aqueous solution. Add Part 2 to Part 1 slowly with continuous mixing at 600 rpm using a Lightnin' Mixer (Model L1003). Keep stirring for another 20 minutes after addition of Part 2 is finished or until a visually uniform emulsion is formed. Homogenize the emulsion for 2-4 minutes using a homogenizer (Greerco Corp., Hudson, N.H.) at a reading of about 30 on a Powerstat Variable Autotransformer (Superior Electric Co., Bristol, Conn.).

Example 63

Non-Aerosol Spray with ADCH Solution

An antiperspirant product can be made using the following ingredients:

Part 1:
36% Phase inversion temperature concentrate ("PIT Concentrate" such as Emulgade® CM from (from Cognis Co., Ambler, Pa.)

Part 2:
1% fragrance; 1% nonionic surfactant (Emulgen L from Cognis Co., Ambler, Pa.)

Part 3:
62% of a composition as described in Example 15

Mix the fragrance and surfactant in a separate beaker to form a clear solution. Add Part 3 and the above solution into Part 1 one after the other at room temperature with continuous stirring until a uniform translucent liquid is formed.

Example 64

Two-Phase Roll-On with ADCH Solution

An antiperspirant product can be made using the following ingredients:

Part 1:
16.30% Cyclomethicone (DC 245 from Dow Corning); 2.80% PPG-3 myristyl ether; 0.80% fragrance Part 2:
69.99% of a composition from Example 14; 9.70% propylene glycol; 0.40% Polyquaternium-10 (Polymer JR, from Amerchol, Edison, N.J.); 0.010% Oleath-10 (Volpo 10 from Croda, Inc., New Jersey)

All of the ingredients for Part 1 are combined in a beaker and the mixture is stirred at 300-400 rpm using a Lightnin' Mixer Model L 1003 until a homogeneous solution is obtained.

Add all the ingredients in Part 2 in a separate beaker together and heat it to 40-50° C. with agitation until a clear solution is obtained.

Add Part 2 to Part 1.

Example 65

Two-Phase Spray with Salt Solution

An antiperspirant product can be made using the following ingredients:

Part 1:
24.00% Cyclomethicone (D5); 5.00% PPG-3 myristyl ether; 1.00% fragrance

Part 2:
65.00% of a composition of Example 15; 5.00% ethanol (Alcohol SD-200 proof (100%))

Mix the ingredients in Part 1 to form a clear solution by using an overhead mixer. Mix the ingredients in Part 2 to form an aqueous solution. Add Part 2 to Part 1.

We claim:

1. A zirconium-free aluminum salt which:
   (a) has an aluminum to chloride molar ratio in the range of 0.5-2.5:1;
   (b) comprises a nitrogen containing buffering material in an amount such that the ratio of nitrogen containing material to aluminum is the range of 0.05-0.26:1 and which nitrogen containing material is selected from the group consisting of a nitrogen containing buffering material of formula

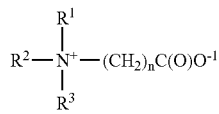

where n is a number in the range of 1-20, and each of $R^1$, $R^2$, and $R^3$ is independently selected from the group consisting of hydrogen, methyl and ethyl; and
   (c) the salt has a pH in the range of 2-4 at a concentration of 15%;
   wherein the salt is free of any other halide scavenging material and has a value of at least 0.50 for the ratio calculated as:

$$\frac{\text{area of Peak 5}}{\text{total area under Peak 2} + \text{Peak 3} + \text{Peak 4} + \text{Peak 5}}.$$

2. A zirconium-free aluminum salt according to claim 1 wherein the ratio of nitrogen containing material to aluminum is in the range of 0.05-0.16:1.

3. A zirconium-free aluminum salt according to claim 1 wherein each of $R^1$, $R^2$, and $R^3$ is methyl.

4. A zirconium-free aluminum salt according to claim 1 wherein the nitrogen containing material is selected from the group consisting of glycine, alanine, serine, glutamine, threonine, valine, leucine and betaine.

5. An antiperspirant composition made with the composition of claim 1.

6. An antiperspirant composition according to claim 5 wherein the composition is a stick comprising a gelling agent which is stearyl alcohol or dibenzylidene sorbitol.

7. An antiperspirant composition according to claim 6 comprising:
   40-55% cyclomethicone; 20-30% stearyl alcohol; 7-15% talc; 15-22% aluminum antiperspirant active added as a powder; optionally 1-3% fragrance.

8. An antiperspirant composition according to claim 5 wherein the composition is a roll-on comprising 45-65% cyclomethicone; 0.1-10% cyclomethicone/dimethicone copolyol; 10-25% in a solution form as 25-45% actives on an anhydrous basis in water; 5-30% water; and optionally 1-3% fragrance.

9. An antiperspirant composition according to claim 5 wherein the composition is a soft solid comprising 40-70% elastomer in cyclomethicone; 5-15% polyethylene; 10-20% C12-15 alkylbenzoate; 0.1-25% antiperspirant active added in powder form 1-15% dimethicone (100 centistokes); and optionally 1-3% fragrance.

10. An antiperspirant composition according to claim 5 wherein the composition is a gel comprising 5-50% cyclomethicone; 0.1-10% cyclomethicone/dimethicone copolyol; 0-10% hydrogenated polyisobutene 250; 0-10% C12-15 alkylbenzoate; 0-10% dimethicone (100 centistokes); 0.1-25% antiperspirant active added in powder form or 10-25% of antiperspirant active added as a solution of 25-45% actives on an anhydrous basis; 5-50% water; and optionally 1-3% fragrance.

11. An antiperspirant composition according to any one of claims 5-10 wherein the glycol content is less than 1.0 weight %.

* * * * *